United States Patent [19]

Finkelstein et al.

[11] Patent Number: 4,899,758
[45] Date of Patent: Feb. 13, 1990

[54] METHOD AND APPARATUS FOR MONITORING AND DIAGNOSING HYPERTENSION AND CONGESTIVE HEART FAILURE

[75] Inventors: Stanley M. Finkelstein, St. Louis Park; Jay N. Cohn, Minneapolis, both of Minn.

[73] Assignee: Regents of the University of Minnesota, Minneapolis, Minn.

[21] Appl. No.: 228,820

[22] Filed: Aug. 2, 1988

Related U.S. Application Data

[63] Continuation of Ser. No. 824,629, Jan. 31, 1986, abandoned.

[51] Int. Cl.$^4$ ............................................... A61B 5/02
[52] U.S. Cl. ................................ 128/672; 364/413.03
[56] References Cited

U.S. PATENT DOCUMENTS

| | | | |
|---|---|---|---|
| 4,562,843 | 1/1986 | Djordjerich et al. | 128/672 |
| 4,592,364 | 6/1986 | Pinto | 128/672 |

OTHER PUBLICATIONS

Walsh, T. J., "Computer Analysis of Continuously Recorded BP in Ambulant Hypertensives", *Computers in Cardiology* Conf. 12-14 Sep. 1978, Hanford Col. pp. 39-46.
Milnor, W. R. et al., "A New Method of Measuring Propogation Coefficients & Char. Impedance in Blood Vessels", Circulation Research, vol. 36, May 1975, No. 5, pp. 631-639.
Finkelstein et al. "Vascular Hemodynamic Impedance in CHF", Amer. Jrnl of Cardiology, vol. 55, pp. 423-427 (1985).
Finkelstein, S. Mietal, "Vascular Compliance in CHF", Proc. 7th Annual Conf. of IEEE Engrg in Medicine & Biol., pp. 550-553 (Sep. 27-30, 1985).
Goldwyn, R. et al., "Arterial Pressure Pulse Contour Analysis Via a Mathematical Model for the Clinical Quantification of Human Vascular Properties", Trans. BME, vol. 14, No. 1, Jan. 1967, pp. 11-20.
Blanche, T. B. et al., "Patient Monitoring Enhanced by New Central Station", H P Jrnl., vol. 31, No. 11, Nov. 1980 pp. 3-11.

*Primary Examiner*—Francis Jaworski
*Attorney, Agent, or Firm*—Merchant, Gould, Smith, Edell, Welter & Schmidt

[57] ABSTRACT

Apparatus and method for monitoring and diagnosing CHF and hypertension includes digitizing brachial artery pulses and determining $C_2$ from modified Windkessel model. CHF and hypertension are monitored and diagnosed by tracking $C_2$ values and testing values against a disease discriminating threshold of 0.08 ml/mm Hg.

15 Claims, 4 Drawing Sheets

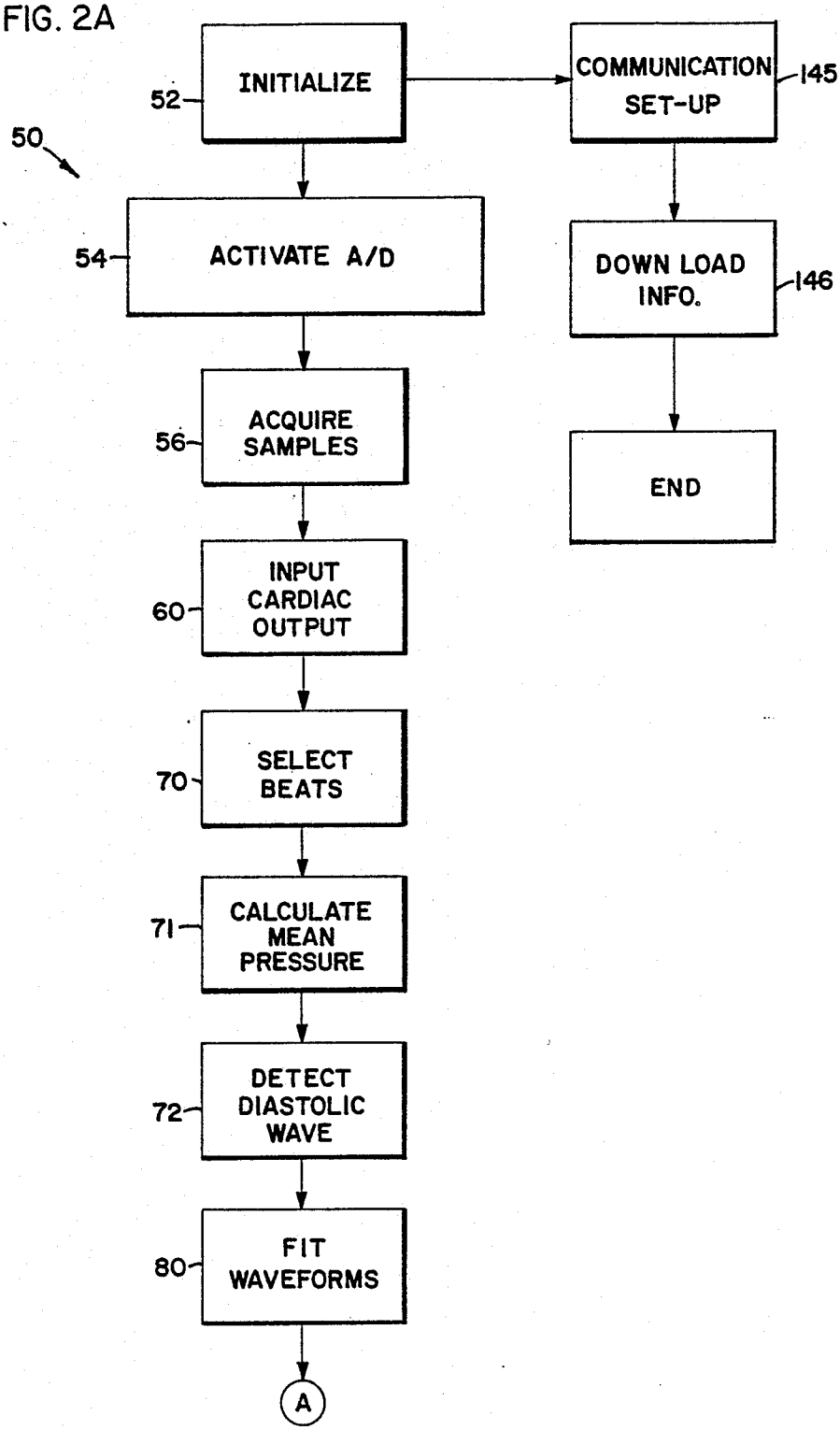

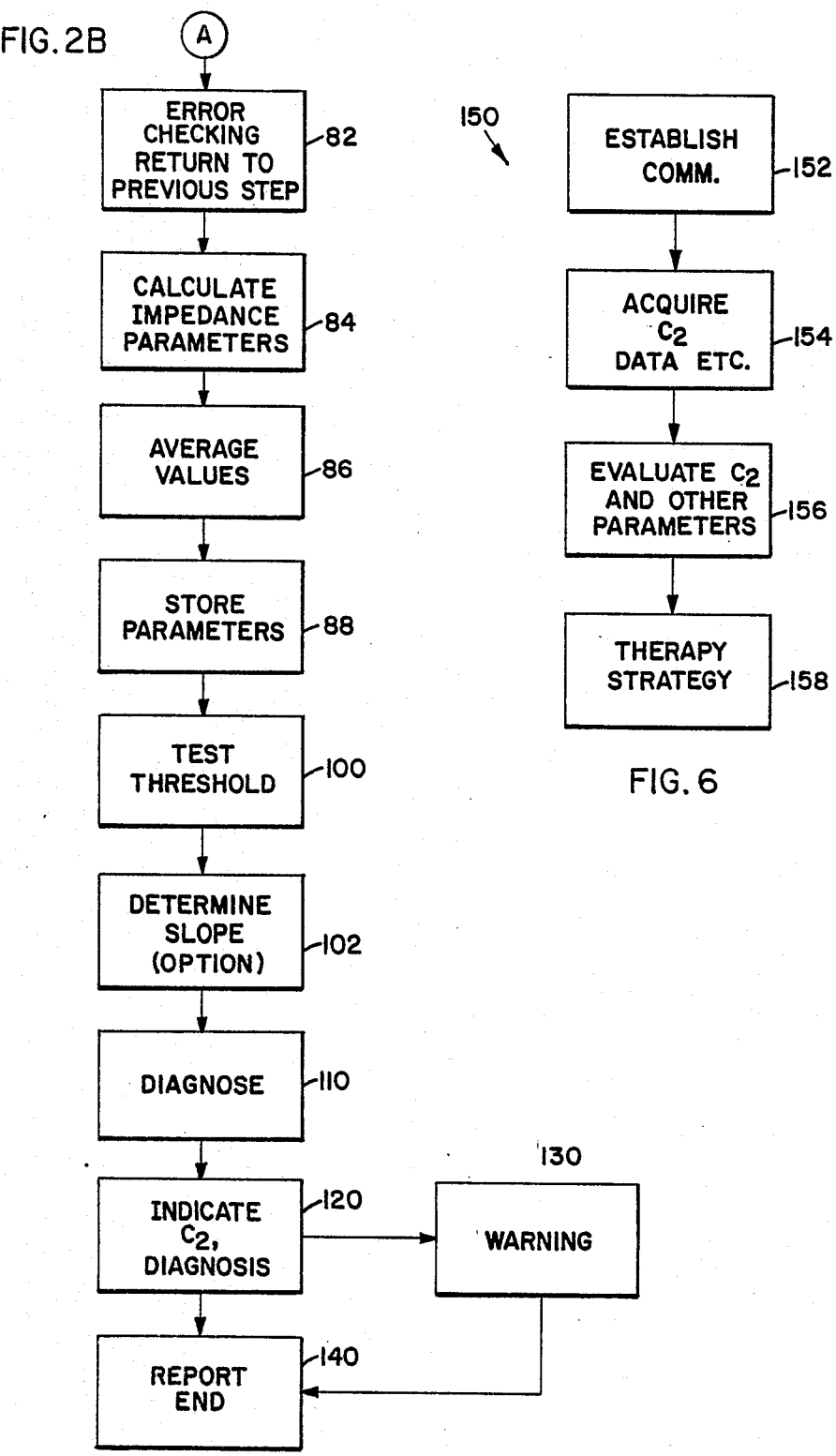

METHOD AND APPARATUS FOR MONITORING AND DIAGNOSING HYPERTENSION AND CONGESTIVE HEART FAILURE

The following invention was made with the support of Grant HL 17871 from the National Institute of Health. The Government has certain rights in the invention.

This is a continuation, of application Ser. No. 824,629, filed Jan. 31, 1986, now abandoned.

TECHNICAL FIELD OF THE INVENTION

The present invention pertains generally to cardiac medicine and more particularly to the diagnosis and monitoring of congestive heart failure (CHF) and hypertension in humans.

BACKGROUND OF THE INVENTION

The characteristics of the peripheral vasculature are important in determining arterial pressure and left ventricular performance in patients with congestive heart failure (CHF) and hypertension. Peripheral vascular resistance is the parameter most frequently used to describe the peripheral vascular bed. However, recent studies suggest that frequency-dependent vascular impedance may be a more sensitive indicator of disease and therapeutic response. The determination of this impedance requires Fourier analysis of simultaneously recorded pressure and blood flow waveforms. Heretofore, pressure and waveforms have typically been measured at the ascending aorta, requiring significant system invasion, and thus limiting the usefulness of the procedure as a diagnostic and monitoring tool.

An alternative impedance measurement technique uses the peripheral arterial pressure pulse contour and a measure of cardiac output to derive vascular impedance properties. This method is minimally invasive, requiring only a brachial artery puncture to obtain the peripheral pressure signal, and thus offers the potential of practical clinical use. Proximal compliance, distal compliance, inertance and peripheral resistance are all determinable from the pressure pulse contour and cardiac output. As set forth below, the present invention utilizes the alternative impedance measuring technique to diagnose and monitor the vascular abnormalities and characteristics of hypertension and CHF.

SUMMARY OF THE INVENTION

The present invention provides a vascular impedance monitor for determining distal compliance properties in the diagnosing and monitoring of patients with hypertension and CHF. Pressure transducer means are provided for converting a brachial artery pressure pulse to a corresponding electrical signal. The monitor includes an analog to digital convertor for sampling and digitizing the electrical signal and memory for storing the resultant data series representing a plurality of pressure pulse contours corresponding to individual heartbeats. The monitor also includes means for marking the relevant diastolic portions of each pulse contour, and means for calculating mean arterial pressure from said data series. The monitor further includes means for fitting said series of data points with a third order equation, and for calculating distal compliance from the derived coefficients, mean arterial pressure and cardiac output.

Long-term storage means is also provided and receives said calculated distal compliance values whereby a chronological data base of distal compliance values may be accumulated over a period of days, months or years. Analysis means are further provided for testing stored distal compliance values against a predetermined threshold and for indicating to the user when distal compliance falls below the threshold for disease diagnosis. The upward or downward trend in distal compliance values may also be used in monitoring the progression and treatment of the condition. Means for indicating and reporting the trend or diagnosis to the user or clinician is also provided.

Thus, as described broadly above the present invention provides apparatus and method for monitoring vascular compliance and for diagnosing and monitoring hypertension and CHF. These and other salient features of the invention, including more subtle aspects thereof, are set forth below in more detail in the ensuing specification and drawings.

BRIEF DESCRIPTION OF THE DRAWING

FIGS. 2A and 2B comprise a schematic flow chart of the software of the present invention;

FIG. 6 is a schematic diagram of the software to be used in the clinic computer according to the present invention.

DETAILED DESCRIPTION OF THE INVENTION

Figure 1:
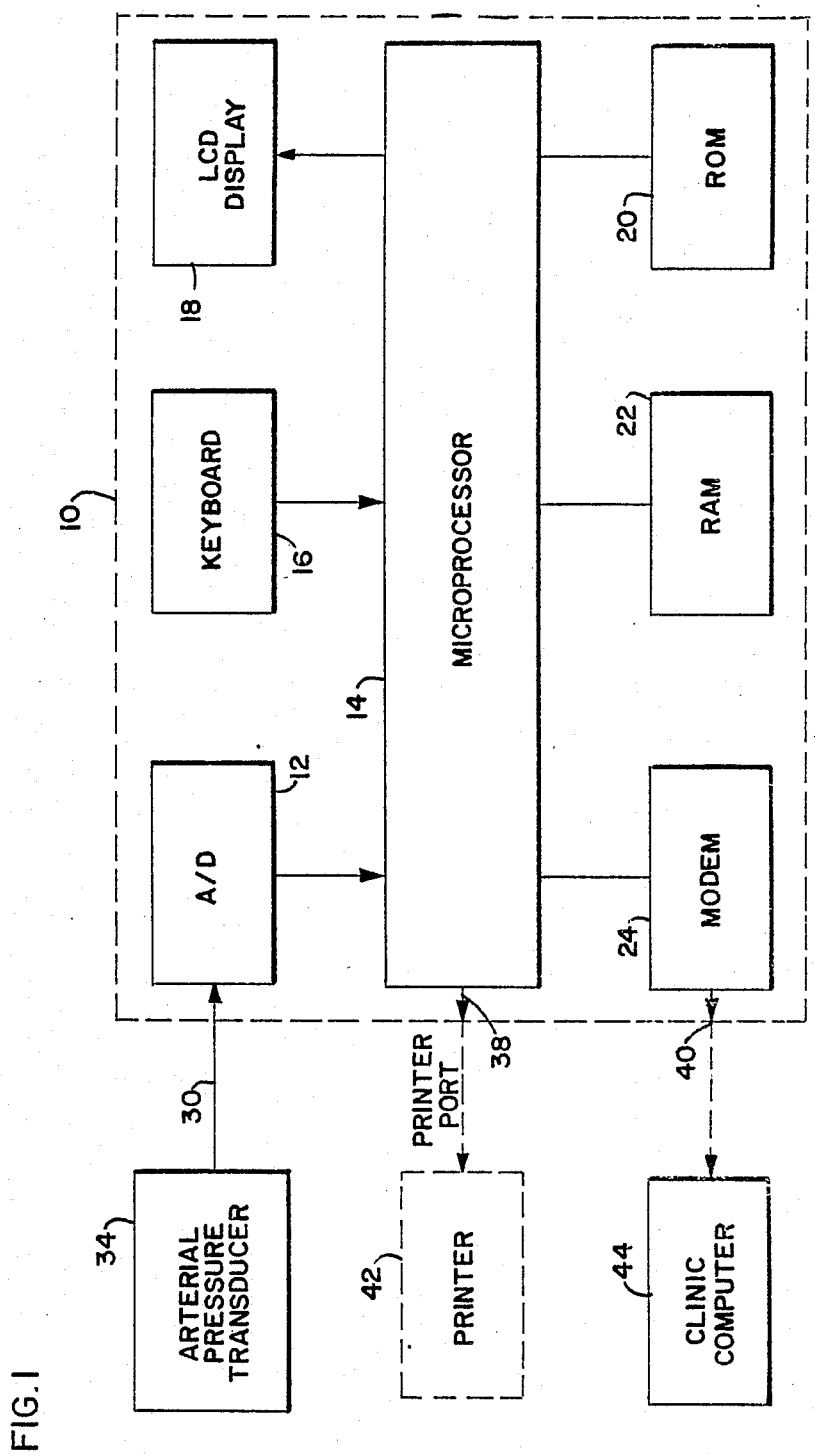
FIG. 1 is a schematic block diagram of the monitor according to the present invention.

The vascular compliance monitor 10 according to the present invention is shown in schematic block diagram form in FIG. 1. The monitor 10 includes an analog to digital convertor (A/D) 12, preferably 12-bit, a microprocessor unit 14, for instance a 6502 model, a keyboard input 16, display 18, ROM 20, RAM 22 and modem 24. An input port 30 is provided to receive analog signal input from an arterial pressure transducer 34. A printer output port 38 and a telephone port 40 are provided from microprocessor 14 and modem 24, respectively.

Transducer 34 is preferably a Statham P23Db pressure transducer, and is preferably connected from its operative position in the brachial artery to port 30 through an 18-gauge, 2-inch Teflon catheter. This catheter-transducer system has an undamped natural frequency higher than 25 HZ and a damping coefficient less that 0.5, providing an acceptable frequency response.

The software component 50 of the monitor 10 is illustrated in block diagram flow-chart form in FIG. 2. Software 10 is maintained in ROM 20 and is referenced by microprocessor 14. Generally speaking, software 50 runs on microprocessor 14 to control the acquisition of artery pressure pulse data, and to process, analyze and diagnose the acquired data.

Figure 3:
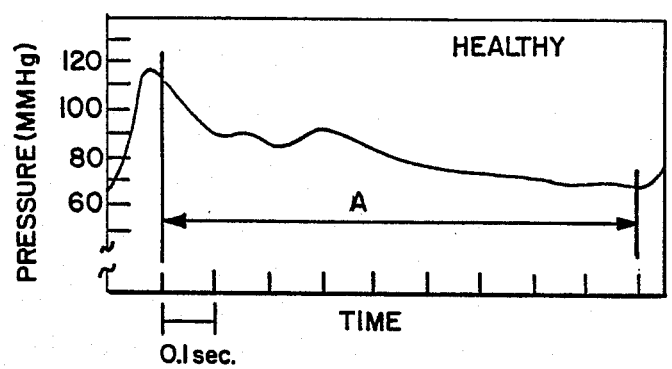
FIG. 3 and 4 are illustrative examples of typical arterial pulse contours in respective healthy and diseased patients.
Figure 4:
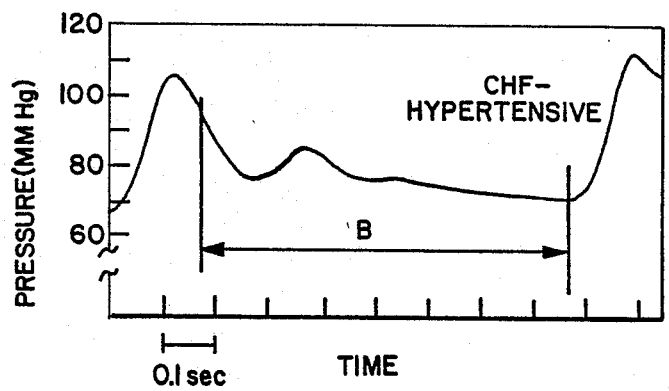

An initialization and mode select routine 52 is provided for initializing microprocessor 14, including prompting the user to enter the date (and other desired patient information). Routine 52 further allows either the monitor mode or communication mode to be selected. If monitor mode is selected, A/D convertor 12 is activated (54) to digitize the analog brachial pressure pulse signal generated by transducer 34 in its position in the patient's brachial artery. Referring to FIGS. 3 and 4, there are illustrated typical brachial artery pulse contours for healthy and CHF or hypertensive patients, respectively.

The present invention uses an A/D sampling rate of 50 samples/second, which is satisfactory to capture the highest frequency components of interest in the brachial pressure pulse. It shall be understood, however, that higher or lower sampling rates may be used, and that the invention is in no way limited to the 50 samples/second rate. Routine 56 provides that the artery is monitored for approximately 30 seconds, producing in the range of 25 to 60 digitized pulses, depending on the heart rate. The stream of digitized pulses are stored in RAM 22 in the form of a continuous series of periodic time dependant data byte samples, with each data byte corresponding to the instantaneous pressure of the artery.

Routine 60 is provided for acquiring a cardiac output value, which is required for calculation of impedance parameters as explained in more detail below. In the present embodiment cardiac output is input directly from keyboard 16 in liters/minute or, alternatively, milliliter/second. Cardiac output may be determined by the thoracic impedance technique using for example the Minnesota Impedance Cardiograph model 30413, with the results being manually transferred to monitor 10. Alternatively, it is contemplated that another noninvasive, inexpensive instrument may be used for this purpose, with the measured output being fed directly into monitor 10 through a microprocessor port.

A selection routine 70 is also provided to analyze the recorded waves and to select a group of six consecutive representative beats preferably of comparatively low noise content. Representative beats are identified by establishing windows of permissible heart rate and mean arterial pressure values whereby abnormally fast or slow heartbeats or high or low pressures can be rejected. The routine can thus pick the series of beats which is most representative. Where possible it is preferable that the windows be tailored to the patient, thus allowing more precise selection of representative beats.

Because only the diastolic portion of each selected beat is of interest, i.e. that part of the pressure wave which corresponds to the period of diastole in the heart, a routine 72 is provided to identify the relevant portions. When marked manually, a clinician can identify the onset of diastole by correlating to the second heart sound S2, and the end of diastole by the upstroke of the following pulse. For example, in FIGS. 3 and 4 diastole is marked by the respective segments A and B. However, for the sake of simplicity the present invention uses a software analysis algorithm to predict and select the segment in each wave most probably corresponding to diastole. Precise detection of onset is generally not critical because the slope of the pulse wave is generally uniform in the range of diastole onset. It is, however, important that the onset of the pulse to be used occurs after the peak in the systolic wave and preferably within twenty milliseconds after the dichrotic notch. Thus, routine 72 searches for the dichrotic notch (not shown in the waves of FIGS. 3 and 4) and marks the onset of diastole immediately thereafter on the wave. The end of diastole in the waveform is easily located by finding the upstroke of the next pulse. With the relevant segments marked the data for each pulse can be analyzed to reveal the vascular impedance properties of the patient.

Figure 5:
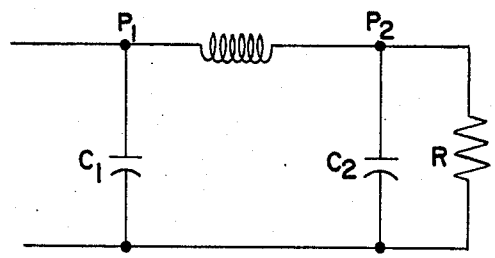
FIG. 5 shows the modified Windkessel model of the arterial system.

The modified Windkessel model of the arterial system is used in the pulse contour analysis of the present invention. As shown in FIG. 5, the model includes components $P_1$, $P_2$, $C_1$, $C_2$, L and R in which:

$C_1$ = proximal compliance (ml/mm Hg)
$C_2$ = distal compliance (ml/mm Hg)
L = inertance (mm Hg/ml/s$^2$)
P1 = proximal arterial pressure (mm Hg)
P2 = brachial artery pressure (mm Hg)
R = peripheral resistance (dynes s cm$^{-5}$)

As taught for example by Goldwyn and Watt in I.E.E.E. Trans. Biomed. Eng. 1967; 14:11–17, the disclosure of which is hereby incorporated by reference herein, $P_2$ of the modified Windkessel model may be represented by the third order equation:

$$P_2(t) = A_1 exp(-A_2 t) + A_3 exp(-A_4 t) cos(A_5 t + A_6),$$

wherein:

$$C_1(mn - p(1/mp)R)$$

$$C_2 = (1/M)(1/R)$$

$$L = (m^2/mn - p)R$$

and wherein:
$m = A_3 + 2 A_5$
$n = 2 A_3 A_5 + A_5^2 + A_6^2$
and
$P = A_3(A_5^2 + A_6^2)$ Thus, knowing R, which can be calculated from cardiac output and mean arterial pressure as follows:

$$R = \frac{\text{mean arterial pressure}}{\text{cardiac output}},$$

$C_1$, $C_2$ and L are readily calculated.

To accomplish the above, software 50 includes routine 80–82, which comprises a modified Gauss-Newton parameter-estimating algorithm as for example referenced by Watt and Burrus in their paper entitled Arterial Pressure Contour Analysis for Estimating Human Vascular Properties", Journal of Applied Physiology, 1976; 40:171–176, the disclosure of which is hereby incorporated herein by reference. Routine 80–82 calculates the optimal values for coefficients $A_1$–$A_6$, using the measured brachial arterial pressure as $P_2(t)$. The algorithm uses an iterative approach which preferably provides fast convergence. The algorithm used in routine 80–82 includes certain modifications. An automatic stopping procedure is included to stop iteration when an acceptable error level in the curve fitting threshold is reached or when convergence slows below a preset threshold. Also, when the process begins to diverge it returns to the previous best case. The routine also includes a weighted iteration interval to improve convergence.

Once the coefficients $A_1$–$A_6$ are established for each pulse contour, the coefficients are used at routine 84 to calculate the $C_1$, $C_2$ and L vascular parameters for each pulse contour. Although all three parameters are calculated in the present embodiment, it shall be understood that the calculation of $C_2$ is the only calculation essential to the operation of the invention. $C_1$, $C_2$ and L are all calculated in accordance with the formulas given above. Once calculated for each pulse contour the calculated values are averaged at routine 86, producing mean values more reliable for accuracy than any individual values. It shall be understood, however, that the averaging process is not essential. For instance, a median value could be selected for use if desired.

After calculation, the $C_2$ (distal compliance) parameter is stored in RAM 22 according to date, preferably in chronological order with parameters determined on previous days. Accordingly, the monitor of the present invention determines the distal compliance value from measured pulse contours from the brachial artery and cardiac output.

Monitor 10 is further operative to analyze the acquired distal compliance values in order to indicate the likelihood or unlikelihood of CHF or hypertension in the patient being monitored. In addition, the monitor is also capable of identifying trends towards or away from the CHF or hypertensive condition, thus allowing for an advance warning to the patient trending toward heart trouble, or indicating a trend toward better cardiac function.

In the present embodiment, diagnostic analyses are performed at the end of each monitoring operation. It is contemplated, however, that diagnosis could be initiated under independent keyboard 16 control if desired. The first diagnostic test performed is preferably a threshold test, performed at routine 100 to determine whether the distal compliance ($C_2$) value is above or below a threshold value.

We have discovered that a $C_2$ threshold value of 0.07 ml/mm Hg is excellent for discriminating between patients with and without CHF. Higher compliance values, i.e. those over 0.07 ml/mm Hg indicate healthy distal compliance and low probability of CHF while values below 0.07 ml/mm Hg indicate probability of CHF. Our discovery further indicates that very low values of $C_2$ 0.03 ml/mm Hg or less), indicate a high probability of CHF. The converse is true such that high values 0.20 ml/mm Hg and above) of distal compliance indicate a very low probability of CHF. Accordingly, it may be desirable to set a relatively high threshold value, for instance 0.10-0.12 ml/mm Hg in order to be overinclusive rather than underinclusive in discriminating the CHF condition. Further information on our discovery can be found in Am J. Cardiol 1985; 55:423-427, the disclosure of which is hereby incorporated herein by reference.

The use of distal compliance ($C_2$) to discriminate between the healthy and hypertensive was suggested by Watt and Burrus in the above-identified paper. The Watt and Burrus paper reported that healthy control patients had typical $C_2$ values of 0.157±0.046 ml/mm Hg while the measured hypertensive subjects had values of 0.024±0.005 ml/mm Hg. Accordingly, the present invention utilizes the peripheral pulse contour analysis method to determine $C_2$ and monitor and diagnose hypertensive subjects.

In the present embodiment of monitor 10 a diagnostic threshold value of 0.08 ml/mm Hg for CHF is preferred, and is used in routine 100 in order to diagnose the likelihood of the CHF condition by testing the measured $C_2$ value against it. A threshold value of 0.08 ml/mm Hg is also used in order to discriminate hypertension. However, it shall be understood that a better discriminating value for hypertension may be determined with experimentation.

Optionally, routines 102 and 110 are also provided for diagnostic purposes, and provide for analyzing distal compliance values accumulated over time to determine the slope or trend of the values over time, for instance over a month or year. Thus, routines 102 and 110 can anticipate a trend toward CHF or hypertension and evaluate the significance or abruptness of the trend. Conversely, a trend away from the threshold can also be determined, indicating recouperation of the heart or improvement of condition, as may result from beneficial therapy. Routine 110 also optionally includes diagnostic logic to evaluate the interrelationship between $C_2$ values and the slope of the values, or other desirable criteria, to provide more sophisticated diagnosis.

Routine 120 is provided to report, at a minimum, the result of the threshold test provided at routine 100, whereby when distal compliance falls below the selected threshold value, a likelihood of CHF or hypertension is indicated. In the case where routines 102 or 110 have been utilized, routine 120 is also provided to report (140) the analysis results either via display 18 or an optional printer 42.

In case the diagnosis indicates a dangerous condition as may be indicated by the $C_2$ value or a dangerous trend as may be indicated for example by a severe distal compliance slope a warning routine 130 is provided to cause monitor 10 to produce a warning indication, either through display 18, or in a printed report (140) to optional printer 42.

Monitor 10 also includes communications capability, whereby accumulated $C_2$ data (or, if desired other stored vascular parameters) may be communicated to further computer equipment 44 in a clinic or hospital, such as a personal computer or minicomputer. Accordingly, monitor 10 may be used by a patient at home with measured and stored parameters particularly $C_2$, being transmitted back to a treating hospital or clinic for review or for further analysis. For this purpose software 50 provides a communications mode including routines 145 and 146, which provide for establishing a communication link with a remote system and for downloading selected information including accumulated $C_2$ values.

As shown in FIG. 1, a clinic or hospital computer 44 is provided to communicate with monitor 10 using a standard modem-telephone link. FIG. 6 illustrates in diagramatic form the software 150 provided for clinic computer 44. A routine 152 is provided for establishing the communication link with monitor 10. Computer 44 preferably includes an auto-answer modem so that monitor 10 may establish communication therewith with a minimum of effort. Data acquisition routine 154 is provided to receive $C_2$ values and other desired data which may be stored in RAM 22, such as cardiac output, mean arterial pressure, $C_1$, L and slope data.

Routine 156 is provided to evaluate $C_2$ and, optionally, other vascular properties. Routine 156 includes all the capabilities described with respect to monitor 10 (routines 100, 102, 110), and preferably more sophisticated analysis techniques which would take into account other known patient data, such as heart failure history. At a minimum, routine 156 provides for a printed report of acquired $C_2$ values which may be reviewed by the treating personnel or physician. Finally, a routine 158 is provided to suggest therapy strategy based on the results of evaluation 156.

Thus, the monitor 10 of the present invention provides a convenient, minimally invasive device to monitor and diagnose, particularly monitor, CHF and hypertensive patients. Also, the device may be employed at remote locations with minimal medical assistance. It is also contemplated that a non-invasive technique may be devised to acquire the brachial artery pressure pulse contour so that the device would be very well adapted to function as a home monitor allowing continuous supervision of chronically ill subjects.

Thus, there has been described above a method and apparatus for monitoring and diagnosing vascular abnormalities in humans. While the invention has been set forth in its preferred form, those skilled in the art will realize that many changes and modifications may be made thereto without departing from the spirit and scope of the invention as set forth in the claims appended hereto.

What is claimed is:

1. A congestive heart failure monitor comprising:
   RAM means for storing data;
   input means for receiving and storing a cardiac output
   transducer means for converting an arterial pressure to a corresponding electrical analog signal;
   analog to digital converter means for receiving said analog signal and digitizing it at a predetermined sampling rate;
   means for storing digitized samples produced by said converter means in said RAM means, said samples being stored over a time interval so that one or more pressure waves, each corresponding to a beat of the human heart, are digitized and stored in said RAM means as a series data bytes, each byte representing the instantaneous pressure of the arterial pressure;
   means for determining a mean arterial pressure value from said stored data bytes and storing said value;
   means for determining the value of the parameter $C_2$ of the modified Windkessel model from the pulse contour of the diastolic portion of said waves and from said stored mean arterial pressure value and said stored cardiac output value;
   means for testing said $C_2$ value against a predetermined threshold value of approximately 0.07 ml/mm Hg indicative of a congestive heart failure condition and identifying a congestive heart failure condition for $C_2$ values below said threshold; and
   means for indicating said identified condition to a user of said vascular compliance monitor.

2. A congestive heart failure monitor comprising:
   RAM means for storing data;
   input means for receiving and storing a cardiac output value;
   transducer means for converting an arterial pressure to a corresponding electrical analog signal;
   analog to digital converter means for receiving said analog signal and digitizing it at a predetermined sampling rate;
   means for storing digitized samples produced by said converter means in said RAM means, said samples being stored over a time interval so that one or more pressure waves, each corresponding to a beat of the human heart, are digitized and stored in said RAM means as a series of data bytes, each byte representing the instantaneous pressure of the arterial pressure;
   means for determining a mean arterial pressure value from said stored data bytes and storing said value;
   means for determining the value of the parameter $C_2$ of the modified Windkessel model from the pulse contour of the diastolic portion of said waves and from said stored mean arterial pressure value and cardiac output value;
   means for storing a plurality of $C_2$ values from a plurality of individual determinations done at successive times by said means for determining whereby a plurality of $C_2$ values may be accumulated over a period of time;
   means for determining the slope of said stored accumulated $C_2$ values over time;
   means for inspecting said slope and determining if said accumulated $C_2$ values are trending upward or downward and identifying a deteriorating CHF condition if said slope is negative and identifying an improving CHF condition if said slope is positive; and
   means for indicating the identified improving or deteriorating condition to the user of said monitor whereby congestive heart failure may be monitored.

3. A monitor according to claim 1 or 2 wherein said transducer means is connected for converting a brachial artery pressure.

4. A method of diagnosing congestive heart failure, comprising the steps of:
   (a) obtaining a cardiac output value;
   (b) measuring arterial pressure using a transducer, said transducer producing an electrical analog signal corresponding to said arterial pressure;
   (c) sampling said analog signal over time at a predetermined sampling rate to provide a series of values representing one or more pressure waves each corresponding to a beat of the human heart;
   (d) determining the mean arterial pressure from said series of values;
   (e) determining the value of the parameter $C_2$ of the modified Windkessel model from the pulse contour of the diastolic portion of said one or more waves as represented by said series of values and from said mean arterial pressure and cardiac output value; and
   (f) testing said $C_2$ value against a predetermined threshold value below which $C_2$ values are associated with a congestive heart failure condition whereby a CHF condition may be identified.

5. The method of claim 4 wherein the predetermined threshold value is approximately 0.07 ml/mm Hg.

6. The method of claim 4 wherein the predetermined threshold value is greater than 0.07 ml/mm Hg to allow for a margin of error in identifying congestive heart failure.

7. A method for monitoring congestive heart failure, comprising the steps of:
   (a) obtaining a cardiac output value;
   (b) measuring an arterial pressure using a transducer, said transducer producing an electrical analog signal corresponding to said arterial pressure;
   (c) sampling said analog signal over time at a predetermined sampling rate to provide a series of values representing one or more pressure waves each corresponding to a beat of the human heart;
   (d) determining the mean arterial pressure from said series of values;
   (e) determining the value of the parameter $C_2$ of the modified Windkessel model from the pulse contour of the diastolic portion of said one or more waves as represented by said series of values and from said mean arterial pressure and cardiac output value;

(f) recording said determining $C_2$ value;

(g) repeating steps (a) through (f) at successive times to accumulate a plurality of recorded $C_2$ values over a period of time;

(h) comparing the first of said accumulated $C_2$ values against a predetermined diagnostic threshold value discriminating between $C_2$ values associated with a healthy condition;

(i) identifying an improving congestive heart failure condition when said first $C_2$ value is below said threshold value and the remaining $C_2$ values are trending toward said threshold value;

(j) identifying an improving healthy trend away from a congestive heart failure condition when said first $C_2$ value is above said threshold value and the remaining $C_2$ values are trending away from said threshold value;

(k) identifying a deteriorating congestive heart failure condition when said first $C_2$ value is below said threshold value and the remaining $C_2$ values are trending away from said threshold value; and (l) identifying a trend toward a congestive heart failure condition when said first $C_2$ value is above said threshold value and the remaining $C_2$ values are trending toward said threshold value.

8. The method of claim 7 wherein the predetermined diagnostic threshold value is approximately 0.07 ml/mm Hg.

9. The method of claim 7 wherein the predetermined diagnostic threshold value is greater than 0.07 ml/mm Hg to allow for a margin of error in identifying a congestive heart failure condition.

10. A method according to claim 4 or 7 wherein said arterial pressure measured is a brachial artery pressure.

11. A method of diagnosing congestive heart failure, comprising the steps of:

(a) obtaining a cardiac output value;

(b) measuring arterial pressure over time to obtain a representation of one or more pressure waves each corresponding to a beat of the human heart;

(c) determining the mean arterial pressure;

(d) determining the value of the parameter $C_2$ of the modified Windkessel model from the pulse contour of the diastolic portion of said one or more waves and from said mean arterial pressure and cardiac output value; and (e) testing said $C_2$ value against a predetermined diagnostic threshold value below which $C_2$ values are associated with a congestive heart failure condition whereby a CHF condition may be identified.

12. A method for monitoring congestive heart failure, comprising the steps of:

(a) obtaining a cardiac output value;

(b) measuring arterial pressure over time to obtain a representation of one or more pressure waves each corresponding to a beat of the human heart;

(c) determining the mean arterial pressure;

(d) determining the value of the parameter $C_2$ of the modified Windkessel model from the pulse contour of the diastolic portion of said one or more waves and from said mean arterial pressure and cardiac output value;

(e) recording said determined $C_2$ value;

(f) repeating steps (a) through (e) at successive times to accumulate a plurality of recorded $C_2$ values over a period of time;

(g) comparing the first of said accumulated $C_2$ values against a predetermined diagnostic threshold value discriminating between $C_2$ values associated with a congestive heart failure condition and those $C_2$ values associated with a healthy condition;

(h) identifying an improving congestive heart failure condition when said first $C_2$ value is below said threshold value and the remaining $C_2$ values are trending toward said threshold value; and (i) identifying an improving healthy trend away from a congestive heart failure condition when said first $C_2$ value is above said threshold value and the remaining $C_2$ values are trending away from said threshold value;

(j) identifying a deteriorating congestive heart failure condition when said first $C_2$ values is below said threshold value and the remaining $C_2$ values are trending away from said threshold value; and (k) identifying a trend toward a congestive heart failure condition when said first $C_2$ value is above said threshold value and the remaining $C_2$ values are trending toward said threshold value.

13. A method according to claim 11 or 12 wherein said arterial pressure is measured from the brachial artery.

14. A method according to claim 11 or 12 wherein said predetermined diagnostic threshold value is approximately 0.07 ml/mm Hg.

15. A method according to claim 11 or 12 wherein predetermined diagnostic threshold value is greater than 0.07 ml/mm Hg to allow for a margin of error in identifying congestive heart failure.

* * * * *

UNITED STATES PATENT AND TRADEMARK OFFICE
CERTIFICATE OF CORRECTION

PATENT NO. : 4,899,758

DATED : February 13, 1990

INVENTOR(S) : Stanley M. Finkelstein et al.

Page 1 of 2

It is certified that error appears in the above-identified patent and that said Letters Patent is hereby corrected as shown below:

Col. 4, line 8, change "P1" to --$P_1$--

Col. 4, line 9, change "P2" to --$P_2$--

Col. 4, line 21, change "C (mn-p(1/mpR)" to --$C_1 = (mn-p(1/mp)(1/R))$--

Col. 4, line 30, change "$m = A_3 + 2A_5$" to --$m = A_2 + 2A_4$--

Col. 4, line 31, change "$n = 2A_3A_5 + A_5^2 + A_6^2$" to --$n = 2A_2A_4 + A_4^2 + A_5^2$--

Col. 4, line 33, change "$P = A_3(A_5^2 + A_6^2)$" to --$p = A_2(A_4^2 + A_5^2)$--

Col. 4, line 44, before "Arte-" insert --"--

Col. 4, line 63, after "vascular" insert --impedance--

Col. 5, line 38, change "$C_2$ 0.03" to --$C_2$(.03--

Col. 5, lines 54 and 55 should be all one paragraph

UNITED STATES PATENT AND TRADEMARK OFFICE
CERTIFICATE OF CORRECTION

PATENT NO. : 4,899,758

DATED : February 13, 1990

INVENTOR(S) : Stanley M. Finkelstein, et al.

It is certified that error appears in the above-identified patent and that said Letters Patent is hereby corrected as shown below:

Col. 6, line 9, change "recouperation" to --recuperation--

Col. 6, line 46, change "diagramatic" to --diagrammatic--

Col. 7, line 21, after "put" insert --value;--

Col. 7, line 31, after "series" insert --of--

Col. 9, line 1, change "determining" to --determined--

Col. 10, line 27 delete "and"

Signed and Sealed this

Seventh Day of January, 1992

Attest:

HARRY F. MANBECK, JR.

*Attesting Officer*     *Commissioner of Patents and Trademarks*